(12) United States Patent
Kritzler

(10) Patent No.: US 7,888,404 B2
(45) Date of Patent: Feb. 15, 2011

(54) BIOSTATIC POLYMER

(75) Inventor: Steven Kritzler, Cronulla (AU)

(73) Assignee: Novapharm Research (Australia) Pty Ltd, Rosebury, New South Wales (AU)

( * ) Notice: Subject to any disclaimer, the term of this patent is extended or adjusted under 35 U.S.C. 154(b) by 0 days.

(21) Appl. No.: 11/883,492

(22) PCT Filed: Feb. 2, 2006

(86) PCT No.: PCT/AU2006/000130

§ 371 (c)(1), (2), (4) Date: Aug. 1, 2007

(87) PCT Pub. No.: WO2006/081617

PCT Pub. Date: Aug. 10, 2006

(65) Prior Publication Data

US 2009/0252701 A9    Oct. 8, 2009

(30) Foreign Application Priority Data

Feb. 2, 2005    (AU)    ............... 2005900444

(51) Int. Cl.
- C09D 5/16 (2006.01)
- B32B 7/12 (2006.01)
- C08K 5/00 (2006.01)
- B01J 13/00 (2006.01)

(52) U.S. Cl. ............ 523/122; 524/186; 524/236; 524/557

(58) Field of Classification Search ......... 523/122; 424/76.1, 78.08, 486, 424, 405; 524/186, 524/236, 557

See application file for complete search history.

(56) References Cited

U.S. PATENT DOCUMENTS

| | | | | |
|---|---|---|---|---|
| 4,885,105 A | * | 12/1989 | Yang et al. | ............ 510/296 |
| 6,270,754 B1 | * | 8/2001 | Zhou et al. | ............ 424/78.08 |
| 2002/0099113 A1 | * | 7/2002 | Rabasco et al. | ............ 523/122 |

FOREIGN PATENT DOCUMENTS

| | | |
|---|---|---|
| GB | 1124120 | 8/1968 |
| JP | 05-163369 A | 6/1993 |
| WO | WO 00/18365 A2 | 4/2000 |

OTHER PUBLICATIONS

Richard J. Lewis, Sr. "Hawley's Condensed Chemical Dictionary, 12th Edition", John Wiley & Sons, Inc., New York pages *** (1993).*
Majumdar et al "Polyvinyl Alcohol: A Taste Sensing Material", Sensors and Actuators B, vol. 114 pp. 747-755 (2006).*
Huggins et al, Spectral Properties of Hydrogen Bonding Systems—systematics of the Infrared Spectral Propertis of Hydrogen Bonding Systesm: Frequency Shift, Half Width and Intensity vol. 60 No. 12 pp. 1615-1619 (1956).*

* cited by examiner

*Primary Examiner*—Basia Ridley
*Assistant Examiner*—Alexander C Kollias
(74) *Attorney, Agent, or Firm*—Wolf, Greenfield & Sacks, P.C.

(57) ABSTRACT

Methods and compositions effective for at least a week for prevention of microbial colony growth on a surface, for example an inanimate surface, where the surface is covered with a dry or substantially dry film formed from a composition comprising a polyvinyl alcohol and a quaternary ammonium compound. The film may be formed in situ by coating the surface with a solution or emulsion comprising a polyvinyl alcohol and a quaternary ammonium compound and then causing or allowing it to dry or substantially dry.

26 Claims, No Drawings

BIOSTATIC POLYMER

RELATED APPLICATIONS

This application is a national stage filing under 35 U.S.C. §371 of international application PCT/AU2006/000130, filed Feb. 2, 2006, which was published under PCT Article 21(2) in English.

FIELD OF THE INVENTION

This invention relates to a polymer composition which is biostatic or biocidal, and to a method for treating a surface to prevent microbial colony growth thereupon. The composition may be formed into a film, and the film will resist microbiological growth for a long period.

BACKGROUND OF THE INVENTION

Any discussion of the prior art throughout the specification should in no way be considered as an admission that such prior art is widely known or forms part of common general knowledge in the field.

It is well known that infection may be transmitted from one person to another by direct contact, by inhalation of air borne infectious particles, or by contact with infectious fluids. Infection is also commonly transmitted indirectly for example by contact with a surface that has itself become infected by contact with an infected person, or with infected airborne particles, or fluids.

For example hospital taps are a notorious for their potential to transmit infection and this has been to some extent alleviated by the use of elbow lever taps. But inside hospitals microbial agents such as bacteria, spores, viruses and fungi can also be indirectly transmitted by staff handling instruments, instrument sterilizing baths, door handles, and by touching many other surfaces. Both inside and outside of hospitals infections are spread via contact with toilet cubicle surfaces, toilet flushing buttons/levers, toilet doorhandles, telephone handsets, lift buttons, furniture and building surfaces, documents, and utensils to name but a few of countless examples. Surfaces of all of these typically harbour significant and rapidly growing colonies of microbes, moulds and the like.

The risk of infection from such like surfaces is reduced by regular cleaning with disinfectant solutions. However it is not practical to wipe such surfaces sufficiently often to provide effective disinfection.

No disinfectants for application to surfaces have been sufficiently durable to maintain a biostatic surface for long periods in use. Attempts to incorporate disinfectants into the surface for slow release have either not proven sufficiently durable, or have not been sufficiently effective or have been too toxic or expensive and none has been commercially successful.

It is an object of the present invention to overcome or ameliorate at least one of the disadvantages of the prior art, or to provide a useful alternative.

BRIEF DESCRIPTION OF INVENTION

According to a first aspect the invention provides a method effective for at least a week for prevention of microbial colony growth on a surface comprising the step of covering the surface with a dry or substantially dry film formed from a composition comprising a polyvinyl alcohol and a quaternary ammonium compound. Preferred embodiments of the invention are effective for at least a week for prevention of microbial colony growth, and in some cases many months.

According to a second aspect the invention provides a composition effective for at least a week for prevention of microbial colony growth on a surface comprising a dry or substantially dry film formed from a composition containing a complex formed between a polyvinyl alcohol and a quaternary ammonium compound.

The present invention provides a polymeric material which can be coated onto a surface from a solution or emulsion and dried or allowed to dry to a dry film, although in less preferred embodiments, the film is substantially dry but may retain some moisture. Preferably, the surface of the film remains biostatic for long periods.

By biostatic is meant that microbial colonies (if any) on the surface do not grow or multiply. By "long periods" in this context is meant a period of at least a week, preferably weeks, months, and more preferably years.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

In preferred embodiments a composition according to the invention is coated onto an inanimate surface (for example a bench top), by being wiped on as a film, or by being sprayed onto the surface. The composition may then be wiped off the inanimate surface and serves to (a) disinfect the surface to which it is applied, (b) cleans the surface and (c) leave a residual transparent residual film which is biostatic for at least a week, and preferably many weeks. The composition need not be wiped off and in the case of for example of an air-conditioning duct interior, the sprayed composition may simply be left to dry. In other preferred embodiments an article may be coated (for example onto sheet material) by knife coating or calendering or spraying or by dipping it into a solution or emulsion of the polymer and drying the film or allowing the film to dry. In preferred embodiments of the invention the quaternary ammonium compound is present in the range of from 0.5% to 75% w/w of the dried composition.

The present inventors have discovered that a combination of a polyvinyl alcohol with from 0.5% to 75% w/w of a quaternary ammonium biocide results in a composition which is biostatic, that is to say on which micro organisms do not grow.

The composition may be used to form a film with which to coat a surface, and which is biostatic and remains so for long periods. The combination may optionally include adhesion promoters, vehicles, pigments and the like.

Desirably, the film forming composition contains one or more surfactants which are selected so as not to deactivate the quaternary ammonium compound and which due to their low surface tension ensure thorough wetting of an underlying inanimate substrate penetrating into any scratches or cracks. Preferred surfactants are selected from non-ionic, cationic or amphoteric surfactants. Conventional formulation wisdom teaches that a combination of a surfactant with a quaternary ammonium compound would deactivate the quaternary compound and/or dry to a sticky surface which attracts dust and other proteinaceous residues which have a tendency to deactivate quaternary ammonium biocides.

The present inventors have discovered that a complex is formed between the polyvinyl alcohol and the quaternary compound which is not sticky in the presence of efficacious levels of quaternary compatible surfactants. Evidence for complex formation resides in a significant shift in the infra red spectrum of a the OH group peak from 3296 $cm^{-1}$ in pure polyvinyl alcohol to 3346 cm$^{-1}$ in mixtures with the quaternary ammonium biocide indicative of very significant levels of hydrogen bonding.

In preferred embodiments the combination is prepared as an aqueous solution which dries to a clear hard film on which micro organisms will not grow. The solution may be applied by wiping, brushing spraying, dipping onto an inanimate surface and drying or allowing drying. Compositions according to the invention may be formed into films for example on door handles, tap handles, toilet seats, telephone handsets, air conditioning ducts, bench tops, or the like.

The term "polyvinyl alcohol" as herein used includes all resins made by the hydrolysis (saponification) of polyvinyl esters, for example polyvinyl acetate. The properties of the resins vary according to the degree of polymerization of the parent polyvinyl ester and the extent of the hydrolysis (saponification degree). In the case of a polyvinyl alcohol prepared from polyvinyl acetate the structure of polyvinyl alcohol may be represented by

—CH$_2$CHOH(CH$_2$CHOH)$_m$— where "1+m" is the degree of polymerization. On partial hydrolysis proportional amounts of residual CH$_2$COO— groups are distributed along the chain in place of OH and the amount of such acetate groups expressed as a percentage is the acetate content. Thus in polyvinyl alcohol of 70% acetate content, 30% of the acetate groups of the original polyvinyl acetate were hydrolysed to hydroxyl groups, and 70% remain as acetate groups. This may be referred to as 70% acetate content or as a 30% alcohol. In grades having above 90% alcohol (less than 10% acetate), the polyvinyl alcohol tends to be only readily soluble in hot water (above 90° C.) although this also varies to an extent with degree of polymerization.

The term "polyvinyl alcohol" as used herein includes all suitable grades, degrees of saponification and degrees of polymerization.

Polyvinyl alcohols may also be made by hydrolysing polyvinyl esters other than acetates, and the same principles apply to the polyvinyl alcohols so formed which may also be used in the invention. However, preferred embodiments of the invention utilize polyvinyl alcohol having an average degree of hydrolysis of greater than 96 mole % hydrolysis, since such compositions are more resistant to removal from a surface to which they are applied by cold or warm water and are less likely to be removed from a treated surface onto the skin by human contact.

Quaternary Ammonium Compounds for Use in the Invention

The invention has been exemplified by reference to n-alkyl dimethyl benzyl ammonium chloride (also known as benzalkonium chloride) as the highly preferred quaternary biocide. Alkyl benzyl quaternary biocidal compounds are preferred; however those skilled in the art will recognise that other biocidal quaternary ammonium antimicrobial compounds may be used in the present invention.

It is preferred that the biocidal quaternary ammonium antimicrobial compound is selected from the group having a general formula:

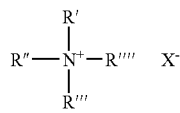

Wherein R' R" R''' R'''' are alkyl radicals that may be the same or different, substituted or unsubstituted, branched or unbranched, and cyclic or acyclic. X is any anion but preferably a halogen, more preferable chlorine or bromine.

Highly preferred antimicrobial compounds are mono-long chain, tri-short chain, tetralkyl ammonium compounds, di-long-chain, di-short chain tetralkyl ammonium compounds and mixtures thereof. By "long" chain is meant about $C_6$-$C_{30}$ alkyl, and by "short" chain is meant $C_1$-$C_5$ alkyl, preferably $C_1$-$C_3$ preferably $C_1$-$C_3$, or benzyl, or $C_1$-$C_3$ alkylbenzyl. Examples include monoalkyltrimethyl ammonium salts such as cetyltrimethyl ammonium bromide (CTAB), monoalkyldimethylbenzyl compounds or dialkylbenzyl compounds. Quat. biocides such as chlorhexadine gluconate may be employed.

The most highly preferred compounds for use in the invention have at least one benzyl radical which may be a substituted benzyl. Examples include $C_8$-$C_{22}$ dimethyl benzyl ammonium chloride, $C_8$-$C_{22}$ dimethyl ethyl benzyl ammonium chloride and di-$C_6$-$C_{20}$ alkyl dimethyl ammonium chloride The quaternary ammonium compound is incorporated for broad spectrum (gram positive and gram negative) antibacterial properties.

Although the quaternary ammonium compound may comprise from 0.5% to 75% w/w of the dried film composition, it is preferred to employ more than 2% w/w of the dried film composition.

Desirably the composition includes one or more surfactants which are compatible with (i.e. do not deactivate) the quaternary ammonium compound. Surfactants selected from non-ionic, cationic and amphoteric surfactants are preferred for example non ionic surfactants such as $C_{12}$-$C_{18}$ straight chain alcohol or ethoxylated alcohols or cocamine oxides. However other examples include branch chain and aromatic ethoxylated surfactants. An example of a suitable cationic surfactant is polyethylene glycol-2-cocamine and an example of a suitable amphoteric surfactant is coco-betaine.

EXAMPLES OF THE INVENTION

Example 1

Manufacture of Composition According to the Invention

A composition was manufactured having the composition shown in table 1:
The following procedure was employed:
About one quarter of the amount of water required (about 724 Kg) was placed into a cleaned and sanitized water jacketed mixing tank.
The mixer was started. Polyvinyl alcohol was added slowly
The temperature was raised to 80-90° C. while stirring
Mixing was continued for another hour or until the Polyvinyl alcohol was dissolved at this temperature.
The tank was then cooled while mixing in the remaining water.
The solution was cooled to below 40° C. and the TERIC® LA8 (Huntsman Corporation, fluidized detergent alcohol alkoxylate) added.
The combination was mixed for 5 minutes and then the quaternary compound (BARQUAT® MB-80 (Lonza, Alkyl ($C_{14}$ 50%, $C_{16}$ 10%, $C_{12}$ 40%) Dimethyl Benzyl Ammonium Chloride)) was added. The combination was stirred for a further 10 mins, the pH adjusted to 7.0 and make up water added as required.

TABLE 1

| composition | | | |
|---|---|---|---|
| Batch size | | 3000 liter | |
| | | 3015 kg | |
| Density | | 1.005 g/mL | |
| Generic name | Trade name | % w/w | (kg) |
| Water | Water | 96 | 2894.4 |
| Polyvinyl alcohol | generic | 1.5 | 45.225 |
| Alcohols, $C_{12}$-$C_{15}$, ethoxylated | Teric LA8 | 0.2 | 6.030 |
| n-Alkyl (40% $C_{12}$, 50% $C_{14}$, 10% $C_{16}$) dimethyl benzyl ammonium chloride (80% solution) | Barquat MB-80 | 1.5 | 45.225 |
| Sodium hydroxide or hydrochloric acid | NaOH (10%) or HCl (10%) | to pH 6.5-7.5 | to pH 7 |
| Water | Water | to 100% | To 3015 kg |

The polyvinyl alcohol has a degree of saponification in the range 80%-95%, more usually about 87.5% and a viscosity of 3.0-3.7 MPa·s(cp)

The composition according to the invention was spread on a metal (aluminium) surface using a knife coater and allowed to dry to form a clear film. The dry film was inoculated with *Pseudomonas Aeruginosa* ATCC 15442 (6.1 log concentration). After 1 hour it was found that the population had reduced to less than 1 log. After 24 hours the population had reduced to zero. After 7 days the population was zero. After 30 days the micro-organism population on the surface was still zero. These tests are ongoing and the inventors are confident that the surfaces will maintain the bacteriostatic properties for a very long period.

The results achieved using *Aspergillus Niger* ATCC16404 were the same or better showing resistance to colonization by both bacteria and fungi.

The same results were achieved by casting films containing only the polyvinyl alcohol and the quat in ratios of from 0.5% up to 75%.

Compositions according to examples 2 and 3 below were also made using the above method with similar results.

Example 2

| | |
|---|---|
| Water | 95.6.0% w/w |
| Polyvinylalcohol | 1.2% w/w |
| (low molecular weight; % hydrolysis 96.5%-99.0%) | |
| Ethoxylated $C_{12}$ to $C_{18}$ straight chain alcohol | 0.2% w/w |
| Benzalkonium chloride | 3.0% w/w |
| Adjust pH to 7.0 with NaOH or HCl | |
| Water | QS 100% |

Example 3

| | |
|---|---|
| Water | 96.0% w/w |
| Polyvinylalcohol | 1.5% w/w |
| (low molecular weight; % hydrolysis 96.5%-99.0%) | |
| Ethoxylated $C_{12}$ to $C_{18}$ straight chain alcohol | 0.2% w/w |
| Benzalkonium chloride | 1.2% w/w |
| Adjust pH to 7.0 with NaOH or HCl | |
| Water | QS 100% |

Films made from compositions according to Examples 1, 2, and 3 were all deemed to be effective for prevention of microbial colony growth in accordance with method AOAC 955.17 after 1, 7, and 30 days.

Example 4

| | |
|---|---|
| Water | 77.5% w/w |
| Polyvinylalcohol | 8.0% w/w |
| (low molecular weight; % hydrolysis 96.5%-99.0% | |
| TericBL8 | 1.0% w/w |
| Benzalkonium chloride | 8.0% w/w |
| Phenoxy ethanol | 1.0% w/w |
| EDTA 4 Na | 0.5% w/w |
| Water | QS 100% |

Biostatic properties of a dry film made from a composition according to example 4 wiped onto an inanimate surface were tested according to ASTM E2180-01 immediately after drying (t=0); after 7 days; and after 30 days with the following results:

| Time (t) | Result |
|---|---|
| 0 | Total kill |
| 7 days | Total kill |
| 30 days | Total kill |

Compositions according to the invention may be coated on and are effective on a wide range of surfaces including without limitation paper, textiles, plastics, metals, glass, and ceramics. These materials may be coated onto articles, (for example paper cups or food containers, or onto other surfaces.

Those skilled in the art will be able to select combinations of polyvinyl alcohols and quaternary ammonium compounds for use in the invention based on the teaching hereof and to select appropriate ratios according to intended end product use. The invention extends to include the combination, solutions of the combination in appropriate solvents, and films formed from the combination with or without solvents.

The claims defining the invention are as follows:

1. A method effective for at least a week for prevention of microbial colony growth on an inanimate surface which is a plastic, metal, glass or ceramic surface, comprising the step of covering the surface with a dry film consisting essentially of a biostatic complex formed by a polyvinyl alcohol with a quaternary ammonium compound, wherein the biostatic complex is effective to reduce a population of *P. Aeruginosa* to less than 1 log within 24 hours, as tested according to the method of ASTM E2180-01, and to maintain the population at less than 1 log for at least 7 days, as tested according to the method of ASTM E2180-01.

2. The method according to claim 1 wherein the dry film is formed in situ by coating the surface with a solution or emulsion consisting essentially of a polyvinyl alcohol with a quaternary ammonium compound, and then causing or allowing the coating to dry.

3. The method according to claim 2, wherein the solution or emulsion further includes a surfactant which does not inactivate the quaternary compound.

4. The method according to claim 3, wherein the surfactant is a non-ionic, cationic or amphoteric surfactant.

5. The method according to claim 3, wherein the surfactant comprises a $C_{12}$ to $C_{18}$ straight chain alcohol or ethoxylated alcohol.

6. The method according to claim 1 wherein the biostatic complex is characterized by a shift in the infrared spectrum of a vinyl alcohol OH group peak from 3296 $cm^{-1}$ to 3346 $cm^{-1}$.

7. The method according to claim 1 wherein the polyvinyl alcohol has a hydrolysis range of greater than 96 mole %.

8. The method according to claim 1 wherein the quaternary ammonium compound comprises from 0.5 to 75 wt. % of the dried film composition.

9. The method according to claim 1 wherein the quaternary ammonium compound is an alkyl benzalkonium compound.

10. The method according to claim 9 wherein the quaternary ammonium compound is n-alkyl dimethyl benzyl ammonium halide.

11. The method according to claim 1, wherein the dry film further consists essentially of a surfactant which does not inactivate the quaternary compound.

12. The method according to claim 11, wherein the surfactant is a non-ionic, cationic or amphoteric surfactant.

13. The method according to claim 11, wherein the surfactant comprises a $C_{12}$ to $C_{18}$ straight chain alcohol or ethoxylated alcohol.

14. A composition for prevention of microbial colony growth on an inanimate surface which is a plastic, metal, glass or ceramic surface, comprising a dry film consisting essentially of a biostatic complex formed by a polyvinyl alcohol with a quaternary ammonium compound, wherein the biostatic complex is effective to reduce a population of *P. Aeruginosa* to less than 1 log within 24 hours, as tested according to the method of ASTM E2180-01, and to maintain the population at less than 1 log for at least 7 days, as tested according to the method of ASTM E2180-01.

15. The composition according to claim 14 wherein the polyvinyl alcohol has an average degree of hydrolysis of greater than 96 mole %.

16. The composition according to claim 14 wherein the quaternary ammonium compound comprises from 0.5 to 75 wt. % of the dried film composition.

17. The composition according to claim 14 wherein the quaternary ammonium compound is an alkyl benzalkonium compound.

18. The composition according to claim 14 wherein the quaternary ammonium compound is n-alkyl dimethyl benzyl ammonium halide.

19. The composition according to claim 14 wherein the biostatic complex is in a solution or emulsion prior to formation of the dry film.

20. The composition according to claim 19, wherein the solution or emulsion further includes a surfactant which does not inactivate the quaternary compound.

21. The composition of claim 14 wherein the biostatic complex is characterized by a shift in the infrared spectrum of a vinyl alcohol OH group peak from 3296 $cm^{-1}$ to 3346 $cm^{-1}$.

22. The composition according to claim 14, wherein the dry film further consists essentially of a surfactant which does not inactivate the quaternary compound.

23. The composition according to claim 22, wherein the surfactant is a non-ionic, cationic or amphoteric surfactant.

24. The composition according to claim 22, wherein the surfactant comprises a $C_{12}$ to $C_{18}$ straight chain alcohol or ethoxylated alcohol.

25. The composition according to claim 22, wherein the surfactant is a non-ionic, cationic or amphoteric surfactant.

26. The composition according to claim 22, wherein the surfactant comprises a $C_{12}$ to $C_{18}$ straight chain alcohol or ethoxylated alcohol.

* * * * *